US010274504B2

(12) United States Patent
Kwon et al.

(10) Patent No.: US 10,274,504 B2
(45) Date of Patent: Apr. 30, 2019

(54) ENCODED MICROCAPSULES AND MICROARRAY FABRICATED THEREFROM

(71) Applicant: SNU R&DB FOUNDATION, Seoul (KR)

(72) Inventors: Sunghoon Kwon, Seoul (KR); Younghoon Song, Seoul (KR); Taehong Kwon, Seoul (KR); Daewon Lee, Seoul (KR); Junhoi Kim, Seoul (KR)

(73) Assignee: QUANTAMATRIX INC., Seoul (KR)

( * ) Notice: Subject to any disclaimer, the term of this patent is extended or adjusted under 35 U.S.C. 154(b) by 40 days.

(21) Appl. No.: 14/064,217

(22) Filed: Oct. 28, 2013

(65) Prior Publication Data

US 2015/0119284 A1 Apr. 30, 2015

(51) Int. Cl.
*G01N 33/50* (2006.01)
*G01N 33/94* (2006.01)
*G01N 33/543* (2006.01)

(52) U.S. Cl.
CPC ......... *G01N 33/94* (2013.01); *G01N 33/5432* (2013.01)

(58) Field of Classification Search
None
See application file for complete search history.

(56) References Cited

U.S. PATENT DOCUMENTS

| 6,340,588 | B1 * | 1/2002 | Nova ............... B01J 19/0046 435/287.1 |
| 6,723,479 | B2 * | 4/2004 | Van De Witte ... B29C 45/14827 156/230 |
| 6,737,216 | B2 * | 5/2004 | Kannurpatti ............. B41C 1/05 430/270.1 |
| 2012/0028834 | A1 * | 2/2012 | Kwon et al. .................... 506/9 |
| 2012/0295297 | A1 * | 11/2012 | Kwon et al. ................... 435/29 |

OTHER PUBLICATIONS

Song et al. Micro Electro Mechanical Systems (MEMS), 2012 IEEE 25th International Conference on. IEEE, 2012.*
Kim et al. Lab on a Chip 11.2 (2011): 246-252.*
Kaczmarek et al. (The Open Process Chemistry Journal 1.1 (2008); pp. 8-11).*
Park et al. (Microfluid Nanofluid (2012) 13:511-518; published online May 19, 2012).*
Kwon et al. (Proceedings from 16th International Conference on Miniaturized Systems for Chemistry and Life Sciences Oct. 28-Nov. 1, 2012, Okinawa, Japan).*
Jinhui Wu et al, A sandwiched microarray platform for benchtop cell-based high throughput screening, Biomaterials 32 (2011) 841e848.
Eun HaeOh et al, Cell-based high-throughput odorant screening system through visualization on a microwell array, Biosensors and Bioelectronics 53 (2014) 18-25.
Stefan J. Pastine et al, Chemicals on Demand with Phototriggerable Microcapsules, J. Am. Chem. Soc. vol. 131, No. 38, 2009, 13586-13587.
Philipp W. Chen et al, Designer Polymer-Based Microcapsules Made Using Microfluidics, Langmuir 2012, 28, 144-152.
Shin-Hyun Kim et al, Double-emulsion drops with ultra-thin shells for capsule templates, Lab Chip, 2011, 11, 3162-3166.
Eric Brouzes et al, Droplet microfluidic technology for single-cell high-throughput screening, PNAS, Aug. 25, 2009, vol. 106 No. 34, 14195-14200.
Cheong Hoon Kwon et al, Drug-Eluting Microarrays for Cell-Based Screening of Chemical-Induced Apoptosis, Anal. Chem. XXXX, XXX, 000-000.
Jin-Woong Kim et al, Fabrication of Monodisperse Gel Shells and Functional Microgels in Microfluidic Devices, Angew. Chem. Int. Ed. 2007, 46, 1819-1822.
Choong Kim et al, Generation of core-shell microcapsules with three-dimensional focusing device for efficient formation of cell spheroid, Lab Chip, 2011, 11, 246-252.
Nikolai Gaponik et al, Labeling of Biocompatible Polymer Microcapsules with Near-Infrared Emitting Nanocrystals, NANO Letters 2003 vol. 3, No. 3, 369-372.
Po-Cheng Chen et al, MEMS microwell and microcolumn arrays: novel methods for high-throughput cell-based assays, The Royal Society of Chemistry 2011.
A. S. Utada et al, Monodisperse Double Emulsions Generated from a Microcapillary Device, Science, 2005, vol. 308, pp. 537-541.
Zhiling Zhang et al, Preparation of fluorescence-encoded microspheres in a core-shell structure for suspension arrays, J. Mater. Chem., 2010, vol. 20, pp. 1179-1185.
Sebastian Seiffert et al, Smart Microgel Capsules from Macromolecular Precursors, J. Am. Chem. Soc. 2010, 132, 6606-6609.
Giuseppe Arrabito et al, Solution Processed Micro- and Nano-Bioarrays for Multiplexed Biosensing, Anal. Chem. 2012, 84, 5450-5462.

* cited by examiner

*Primary Examiner* — Tracy Vivlemore
*Assistant Examiner* — Sahana S Kaup
(74) *Attorney, Agent, or Firm* — STIP Law Group, LLC (57) ABSTRACT

Disclosed is a microcapsule encoded depending on the kind of a target substance included therein. The encoded microcapsule has a hydrophilic liquid core including the target substance and a hydrophobic shell surrounding the liquid core. The encoded microcapsule includes graphical codes introduced on the surface of the shell.

17 Claims, 12 Drawing Sheets

ENCODED MICROCAPSULES AND MICROARRAY FABRICATED THEREFROM

FIELD OF THE DISCLOSURE

The present disclosure relates to encoded microcapsules and a microarray fabricated using the same.

BACKGROUND

Drug screening refers to a process to screen substances useful as drugs from various kinds of naturally occurring or artificially synthesized substances and drug candidates by reacting the substances with cells and observing changes of the cells induced by the substances. A great deal of research is currently being conducted around the world on drug screening for the purpose of finding anticancer drugs capable of selectively destroying cancer cells. Recent remarkable developments in genomics, proteomics, and combinatorial chemistry have led to a marked increase in the number of various kinds of drug candidates. However, all drug candidates are difficult to handle by existing drug screening that has been performed on well-plates. Under such circumstances, microfluidics has received considerable attention due to the possibility of greatly reducing the quantity of samples used at one time.

Microcapsules and related technologies thereof are increasingly investigated in various fields, including drug delivery based on the principle that capsules are broken or expand under particular ambient environmental conditions (e.g., temperature and pH) to release substances (e.g., drugs) contained therein to the outside and allow the released substances to react with surrounding substances. Such microcapsule-related technologies are not substantially applied to the field of drug screening. The greatest reason for this is because numerous drug candidates cannot be perfectly handled due to the limited number of codes that can be engraved on microcapsules.

Most current microarray-based drug screening techniques employ spotting drugs on the surface of array chips using suitable equipment, such as inkjet printers, and recognizing coordinates of drug arrays spotted on the chips as codes to match the codes with the drugs. These techniques have an advantage in that small quantities of samples can be used but require the use of expensive equipment. Another troublesome problem associated with an increase in the number of drugs is frequent exchange of the drugs with new ones in the toners of printers.

SUMMARY

One aspect of the present disclosure provides a microcapsule encoded depending on the kind of a target substance included therein, the microcapsule having a hydrophilic liquid core including the target substance and a hydrophobic shell surrounding the liquid core, wherein the encoded microcapsule includes graphical codes introduced on the surface of the shell.

A further aspect of the present disclosure provides a method for producing encoded microcapsules, the method including: preparing double emulsion droplets, each of which has a hydrophilic liquid core including a target substance and a hydrophobic shell surrounding the liquid core and containing a photocurable polymer; curing the photocurable polymer to form core-shell structured microcapsules; and irradiating patterned energy on the cured shells of the microcapsules to form graphical codes.

Another aspect of the present disclosure provides an assay method using microcapsules encoded so as to be distinguished from each other depending on the kind of target substances included therein, the method including: introducing the encoded microcapsules into a substrate with microwells; reading the codes of the encoded microcapsules arranged inside the microwells; introducing analytes into the microwells; and breaking the microcapsules introduced into the microwells to allow the target substances to react with the analytes, wherein each of the microcapsules has a hydrophilic liquid core including the target substance and a hydrophobic shell surrounding the liquid core, and the microcapsule includes graphical codes introduced on the surface of the shell.

Yet another aspect of the present disclosure provides a microarray fabricated by introducing microcapsules, which are encoded so as to be distinguished from each other depending on the kind of target substances included therein, into a substrate with microwells, and breaking the microcapsules assembled in the microwells to release core liquids including the target substances from the microcapsules, wherein each of the microcapsules has a hydrophilic liquid core including the target substance and a hydrophobic shell surrounding the liquid core, and the microcapsule includes graphical codes introduced on the surface of the shell.

BRIEF DESCRIPTION OF THE DRAWINGS

These and/or other aspects and advantages of the disclosure will become apparent and more readily appreciated from the following description of the embodiments, taken in conjunction with the accompanying drawings of which.

DETAILED DESCRIPTION

Embodiments of the present disclosure will now be described in more detail with reference to the accompanying drawings. These embodiments are provided so that this disclosure is thorough, and will fully convey the scope of the disclosure to those skilled in the art. Accordingly, the present disclosure may be embodied in many different forms and should not be construed as limited to the exemplary embodiments set forth herein. In the drawings, the dimensions, such as widths, lengths and thicknesses, of elements may be exaggerated for clarity. The same reference numerals denote the same elements throughout the drawings. The drawings are explained from an observer's point of view. It will be understood that when an element is referred to as being "on" another element, it can be directly on the other element, or one or more intervening elements may also be present therebetween.

Figure 1:
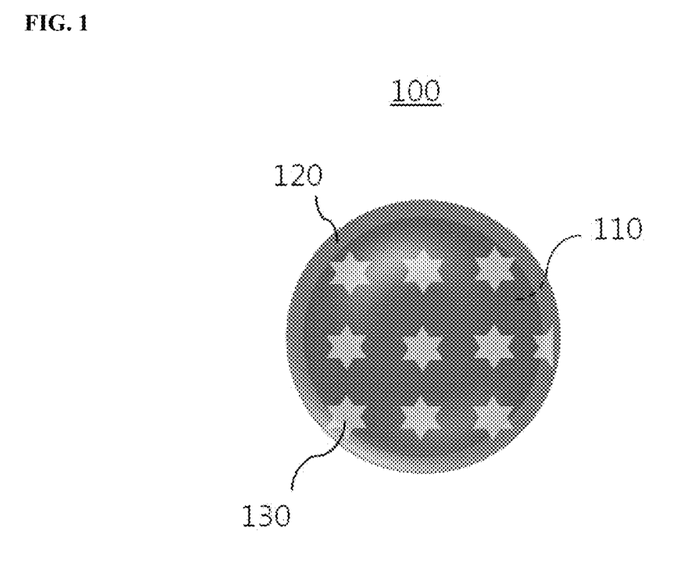
FIG. 1 shows the structure of an encoded microcapsule according to one embodiment of the present disclosure.

FIG. 1 shows the structure of an encoded microcapsule according to one embodiment of the present disclosure.

The encoded microcapsule 100 is encoded so as to be distinguished depending on the kind of a target substance included therein. The encoded microcapsule 100 has a core-shell structure as a whole. Specifically, the encoded microcapsule 100 has a hydrophilic liquid core 110 including a target substance and a hydrophobic shell 120 surrounding the liquid core 110. Graphical codes 130 are introduced on the surface of the shell 120.

The target substance contained in the liquid core 110 of the encoded microcapsule 100 reacts with an analyte later. The target substance may be, for example, a chemical substance or a biological substance. As an example, the chemical substance may be a drug and the biological substance may be selected from the group consisting of cells, molecules, proteins, bacteria, DNAs, RNAs, and combinations thereof.

The core-shell structured encoded microcapsule 100 may be produced from a double emulsion droplet. The double emulsion droplet has a structure in which a smaller droplet is included in an emulsion droplet. For example, an oil droplet may be present in a water droplet (o/w/o) and a water droplet may be present in an oil droplet (w/o/w). The double emulsion droplet may be prepared through two emulsification steps using general emulsifying devices. Alternatively, the double emulsion droplet may be prepared using a microfluidic chip. The inner and outer droplets of the double emulsion droplet form the liquid core 110 and the shell 120, respectively.

The liquid core 110 may be composed of any hydrophilic medium that can dissolve or disperse the target substance. The liquid core 110 may be a biocompatible material. The biocompatible material may be water or an alcohol. A preferred form of the liquid core 110 is a water droplet.

The diameter of the liquid core 110 is not particularly limited and may be from about 50 to about 500 nm.

The shell 120 maintains the shape of the liquid core 110 while surrounding the liquid core 110. The shell 120 may be formed by curing a photocurable polymer. Examples of suitable photocurable polymers include silicon-containing polymers and acrylic polymers. For enhancement of hydrophobicity, hydrogen atoms in the chains of the photocurable polymer may be substituted with fluorine groups or the photocurable polymer may be copolymerized with a fluorine-containing polymer. For example, the photocurable polymer may be a liquid Teflon material. A specific example of the photocurable polymer may be perfluoropolyether-urethane dimethacrylate. The shell 120 is formed by curing the photocurable polymer contained in the outer droplet of the double emulsion droplet. The outer droplet further includes a photoinitiator. The photoinitiator initiates the curing of the photocurable polymer by an external energy source, for example, ultraviolet light, to form the shell 120. The thickness of the shell 120 is not specially limited and may be about 5 to about 50 µm.

The graphical codes 130 may consist of characters or figures. Conventional techniques for engraving codes on microcapsules are primarily based on spectral coding. According to spectral coding, several kinds of fluorescent materials, like fluorescent dyes or quantum dots, are mixed with a material forming a capsule or a material intended to be contained in a capsule, and the ratios of the fluorescent intensities of the fluorescent materials are used as codes. Spectral coding using fluorescent intensity ratios as codes is greatly limited in its application to various drug candidate groups necessary for drug screening, etc. because the number of expressible codes is very limited. Further, mixing of a fluorescent material with a target substance in a capsule may affect the state of a core material of the capsule.

The graphical codes 130 may contain a fluorescent material. The fluorescent material may be one derived from a photoinitiator having a chromophore. For example, when a patterned energy source is irradiated to engrave the graphical codes 130 on the shell 120, the fluorescent intensity of the photoinitiator contained in the irradiated regions of the shell is increased.

Figure 2:
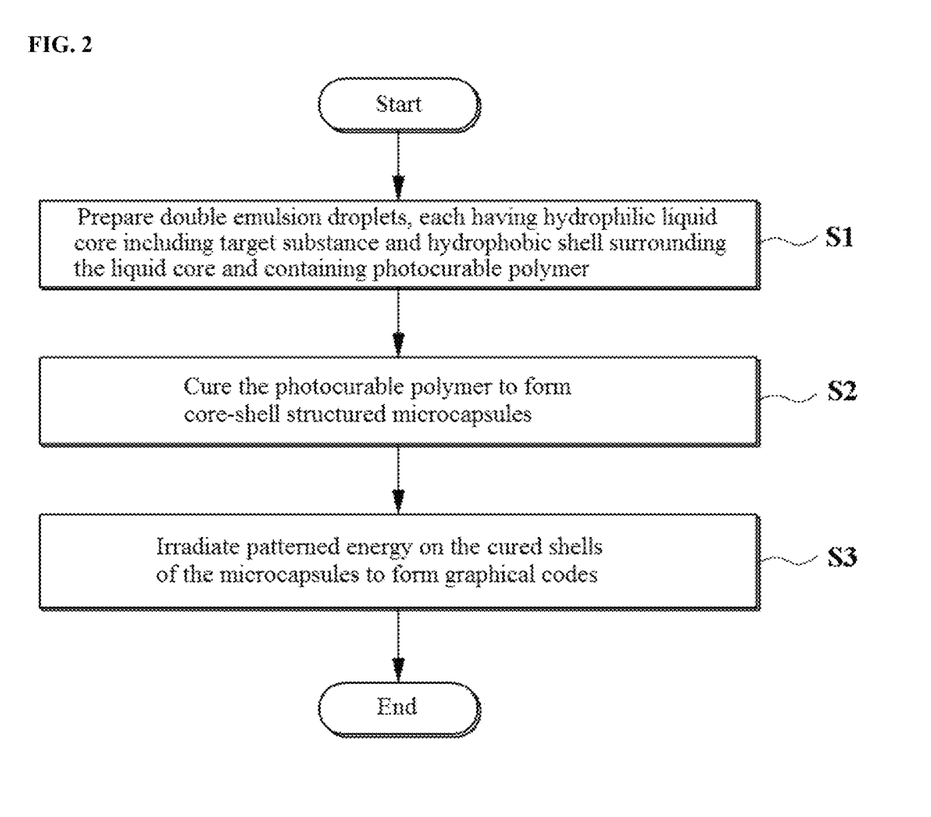
FIG. 2 is a flow chart showing a method for producing encoded microcapsules according to one embodiment of the present disclosure.

According to a further embodiment of the present disclosure, a method for producing encoded microcapsules is provided. FIG. 2 is a flow chart showing a method for producing encoded microcapsules according to one embodiment of the present disclosure.

Referring to FIG. 2, in step S1, double emulsion droplets are prepared. Each of the double emulsions droplets has a hydrophilic liquid core including a target substance and a hydrophobic shell surrounding the liquid core and containing a photocurable polymer. A material for shell portions of the microcapsules may be a hydrophobic material, for example, a liquid Teflon material. Various hydrophilic materials may be used to form core portions of the capsules.

In step S2, the photocurable polymer is cured to form core-shell structured microcapsules. The photocurable polymer may be cured by ultraviolet light. As a result of the curing, the core liquid is encapsulated by the solidified shells.

In step S3, patterned energy is irradiated on the shells of the microcapsules to form graphical codes.

The hydrophobic shells may contain a photoinitiator whose fluorescence properties are enhanced upon irradiation with the patterned energy source. The photoinitiator used in the present disclosure is decomposed upon irradiation with ultraviolet light. Some of the photodecomposition products cure the photocurable polymer through radical reactions and some thereof exhibit fluorescence properties. A higher intensity of ultraviolet light leads to a higher degree of photodecomposition of the photoinitiator, which increases the amount of photodecomposition products with fluorescence properties, thus bringing about an increase in fluorescent intensity. The photoinitiator is used for photocuring and encoding. For example, the amount of the photoinitiator mixed with the photocurable polymer may be from 1 to 5% by weight, based on the total weight of the shells. Within this range, the capsules can be solidified and also be encoded by ultraviolet light.

Examples of materials suitable for use as the photoinitiator are not particularly limited. The photoinitiator may be any material that has both a moiety capable of being decomposed by an external energy source and a chromophore capable of emitting fluorescence after decomposition. The photoinitiator is preferably 2,2-dimethoxy-2-phenylacetophenone.

The double emulsion droplets may be prepared using a microfluidic chip including a channel area having a hydrophobic surface and a channel area having a hydrophilic surface. The microfluidic chip may be made of, for example, polydimethylsiloxane (PDMS). Specifically, the microfluidic chip may be made by the following procedure. First, liquid PDMS is poured onto a silicon wafer that is microfluidic chip-patterned with a photoresist using photolithography and thermally cured. After curing, the cured PDMS is peeled off from the wafer and the two PDMS microfluidic chips are aligned and bonded after oxygen plasma treatment to complete the construction of the microfluidic chip.

Ultraviolet light, visible light, infrared light, and electron beam may be used without limitation as the patterned energy for the formation of the graphical codes. The graphical codes may be formed by lithography. For example, ultraviolet light as the patterned energy may be irradiated through a physical mask or a digital micromirror device (DMD).

Figure 3:
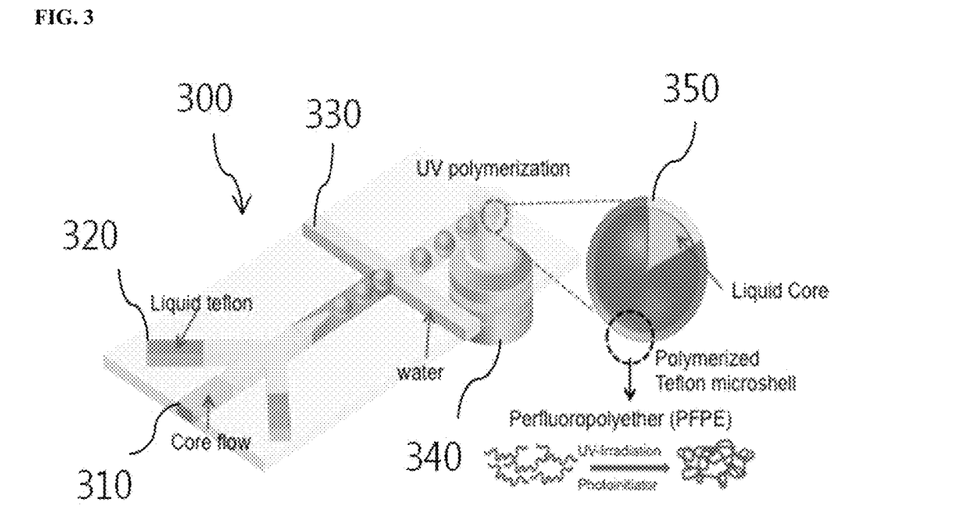
FIG. 3 is a diagram showing the production process of microcapsules using a microfluidic chip.

FIG. 3 is a diagram showing the production process of the microcapsules using a microfluidic chip. Referring to FIG. 3, the microfluidic chip 300 includes a fluidic channel 310 for the formation of inner droplets, a fluidic channel 320 for the formation of outer droplets, and an outermost fluidic channel 330.

The outermost fluidic channel 330 of the microfluidic chip 300 may be hydrophilically coated in order to produce the microcapsules in the form of water/oil/water double emulsion droplets. For example, the surface of the channel 330 may be made hydrophilic by introducing a hydrophilic coating material composed of 2-[methoxy(polyethyleneoxy)propyl]trimethoxysilane as a silane coupling agent and toluene in a volume ratio of 1:9 into the outermost fluidic channel 330 to adhere the coating material to the channel 330 of the microfluidic chip 300.

After hydrophilic coating of the outermost fluidic channel 330, a core fluid is allowed to flow from the fluidic channel 310 for the formation of inner droplets under a flow of water. The core fluid is cut by liquid Teflon (e.g., a PFPE photocurable polymer) as a fluid of the fluidic channel 320 for the formation of outer droplets to form inner droplets. The fluid for the formation of outer droplets further includes a photoinitiator to cure the liquid Teflon. The core fluid may be water containing a target substance. The inner droplets are again cut by water of the outermost fluidic channel 330 to form double emulsion droplets in which the inner droplets are included in the outer droplets. The size of the double emulsion droplets may be controlled by varying the sizes of the microfluidic chip channels 310, 320 and 330. Thereafter, the liquid Teflon material is cured by irradiation with ultraviolet light from an external light source 340 to form polymerized Teflon microshells, completing the production of solidified microcapsules 350, each of which includes the liquid core. Each of the microcapsules 350 contains the target substance such as a drug. The target substance can be stably stored inside the capsules 350 for a long time of at least 30 days without escaping from the capsules 350.

Figure 4:
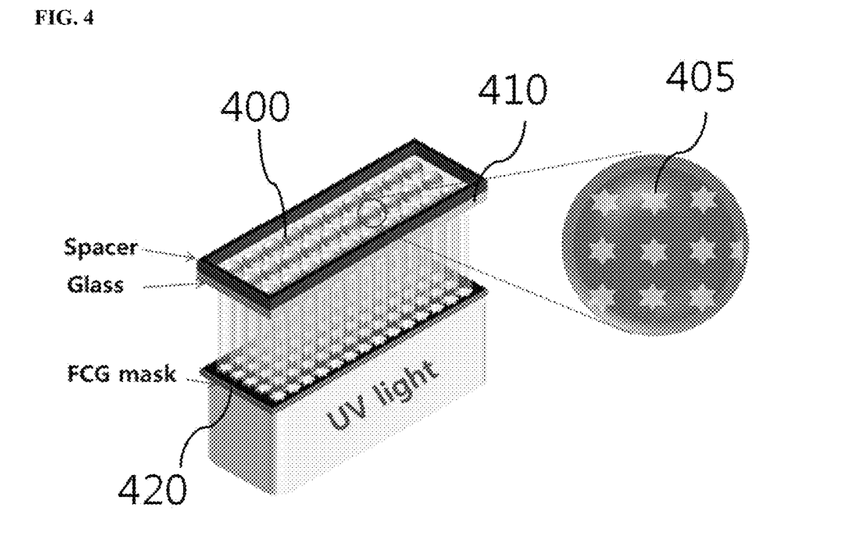
FIG. 4 is a diagram showing the encoding process of microcapsules using a patterned mask and ultraviolet light.

FIG. 4 is a diagram showing the encoding process of microcapsules using a patterned mask and ultraviolet light. Referring to FIG. 4, the solidified microcapsules 400 are placed on a transparent substrate 410 to form a single layer, followed by irradiation with patterned ultraviolet light through a mask 420 to engrave codes 405 on the shell portions of the microcapsules. The codes 405 have the same pattern as the mask pattern. The codes 405 may be locally formed through a light focusing lens. Alternatively, the codes 405 may be formed over a large area by irradiation with parallel light through the mask 420. For example, the microcapsules may be encoded using 2,2-dimethoxy-2-phenylacetophenone (DMPA) as a photoinitiator for photocuring, which is mixed with a liquid Teflon polymer. This encoding is based on the principle that the fluorescence properties of DMPA increase as the intensity of ultraviolet light irradiated increases. The fluorescent intensity of the codes may vary depending on the concentration of the photoinitiator mixed with the polymer and the intensity of ultraviolet light, and the pattern of the codes may vary by changing the mask pattern.

Figure 5:
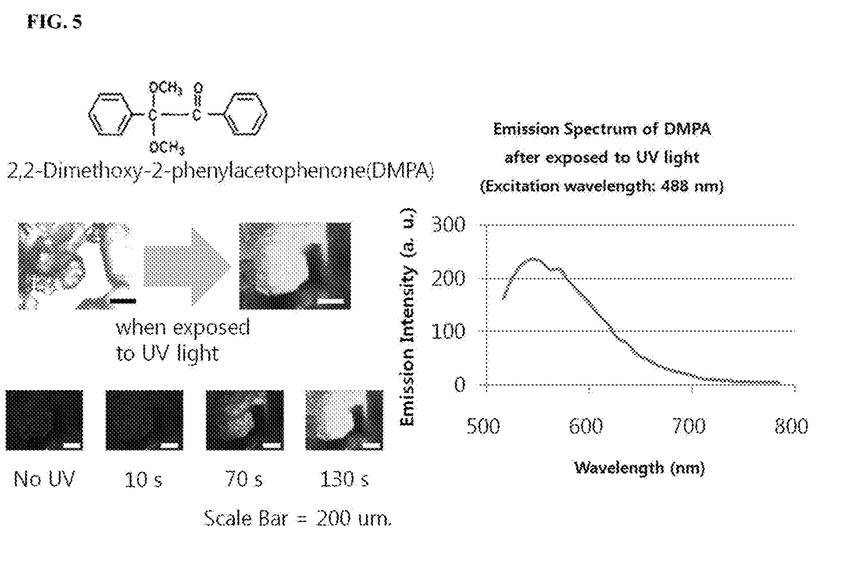
FIG. 5 shows fluorescence properties of DMPA as a photoinitiator upon irradiation with ultraviolet light.

FIG. 5 shows the fluorescence properties of DMPA as a photoinitiator upon irradiation with ultraviolet light. The left images of FIG. 5 are fluorescent images of the photoinitiator in the form of a solid when ultraviolet light was irradiated on the photoinitiator. As can be seen from the images, the photoinitiator had no substantial fluorescence properties when no ultraviolet light was irradiated thereon, and the intensity of fluorescence observed in the solid photoinitiator increased with increasing ultraviolet irradiation time. The right graph of FIG. 5 is an emission spectrum of the solid photoinitiator after exposed to ultraviolet light. The peak fluorescent intensity of the photoinitiator was observed in the wavelength band of about 550 nm, which is similar to the wavelength band in which the peak fluorescent intensity was observed in the fluorescence spectrum of the material extracted by column chromatography.

Figure 6:
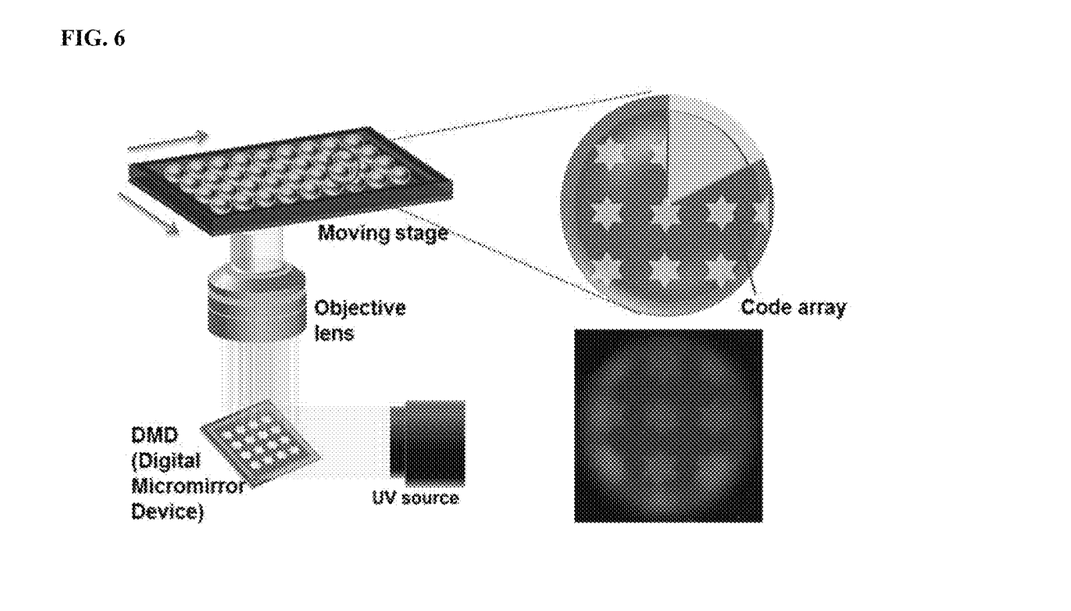
FIG. 6 shows an encoding process using a digital micromirror device (DMD)

FIG. 6 shows an encoding process using a digital micromirror device (DMD). Referring to FIG. 6, the digital micromirror device (DMD) includes a micrometer-sized mirror array that is electrically driven to regulate the angles of the mirrors. The DMD can reflect only desired patterned light toward desired locations due to its ability to individually regulate the angles of the mirrors. By using the DMD, codes of various patterns and characters can be easily engraved. A combination of the DMD and an objective lens can focus ultraviolet light from a UV source to locally engrave patterns on desired locations. An automated moving stage is driven to enable encoding on a large area. The bottom right inset of FIG. 6 is a fluorescent image of an actually encoded microcapsule captured using an optical microscope. The optical microscopy image shows a code array of the finally encoded microcapsule.

Figure 7:
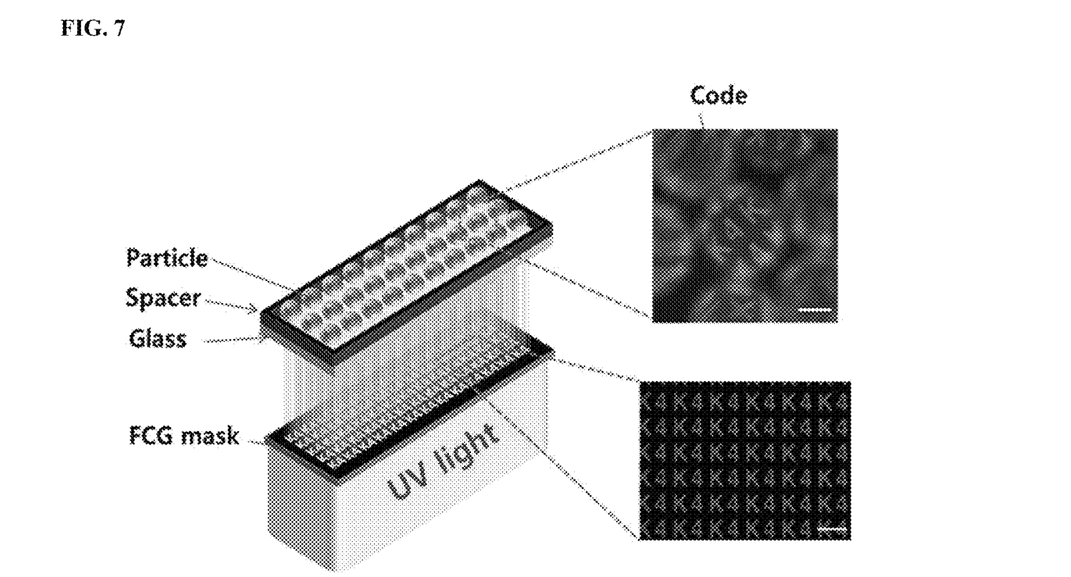
FIG. 7 shows a large-area encoding process using a film-combined glass (FCG) mask.

FIG. 7 shows a large-area encoding process using a film-combined glass (FCG) mask. Referring to FIG. 7, The FCG mask is a combination of a patterned film and transparent glass. The size of the mask is controllable. After the microcapsules are placed on the FCG mask, ultraviolet light is irradiated from the bottom of the mask. The ultraviolet light passes through transparent patterned portions of the mask to engrave codes on the microcapsules. The codes have the same pattern as the mask pattern. A larger size of the mask leads to an increase in the number of the microcapsules on which codes can be engraved at one time, achieving large-size encoding.

Figure 8:
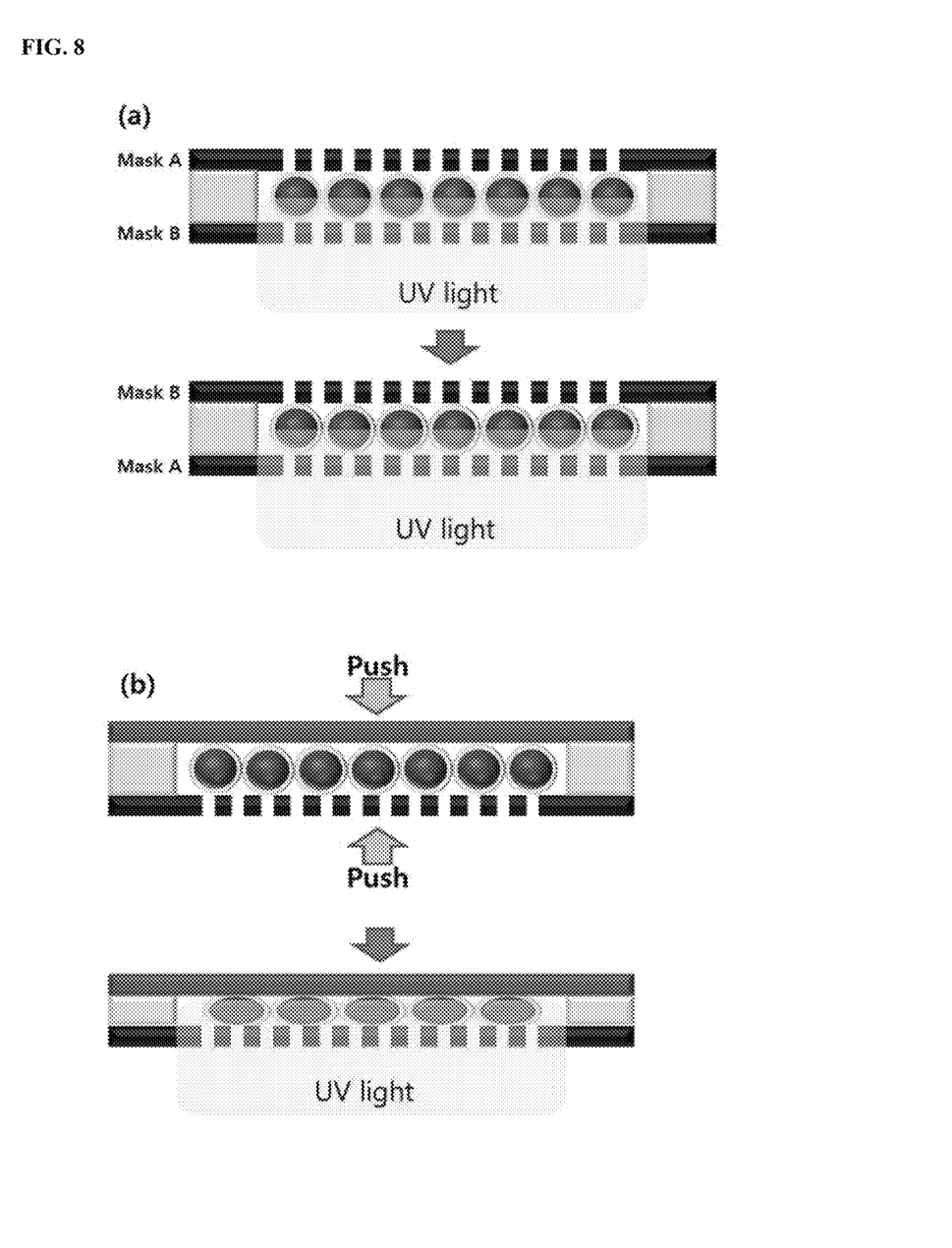
FIG. 8 shows two methods for bi-directional encoding of microcapsules.

On the other hand, after the microcapsules are placed, they may be irradiated with ultraviolet light only from one direction. In this case, codes are easily engraved on the shell portions of the capsules close to the mask but are not substantially engraved on the opposite shell portions of the capsules. The ultraviolet light should be transmitted through the microcapsules to engrave codes on the opposite shell portions. In actuality, the ultraviolet light spreads before reaching the opposite sides. In attempts to solve this problem, two methods are proposed. FIG. 8 shows two methods for bi-directional encoding of the microcapsules.

In one embodiment, the patterned energy may be irradiated in a bi-directional encoding manner using two masks interposing the microcapsules therebetween (see (a) of FIG. 8). According to this method, the two masks are placed on both upper and lower sides of the microcapsules and are irradiated with ultraviolet light. The ultraviolet light may be irradiated from both top and bottom. Alternatively, the ultraviolet light may be irradiated from only one direction. In this case, a substrate on which the capsules are placed is turned over such that both sides of the substrate are exposed to the ultraviolet light equally.

In a further embodiment, the patterned energy may be irradiated in such a manner that a mask and a planar substrate are arranged to face each other through the microcapsules, pressed to each other, followed by bi-directional encoding (see (b) of FIG. 8). According to this method, the microcapsules are placed between the mask and the planar substrate, and upward and downward pressures are applied simultaneously to make the microcapsules flat, so that the ultraviolet light irradiated through the shell portions of the capsules close to the mask reaches the opposite shell portions before spreading.

The bi-directional encoding methods have an advantage in that codes of the microcapsules can be observed even though the microcapsules are rotated in undesired directions. For example, in the case where each microcapsule is encoded in only one direction, the microcapsule is half rotated, and the unencoded side is located close to a microscope, it is difficult to observe the codes of the microcapsule. In contrast, when codes are engraved in both directions, all sides of each microcapsule have the codes that can be observed irrespective of the rotational direction of the microcapsule.

Figure 9:
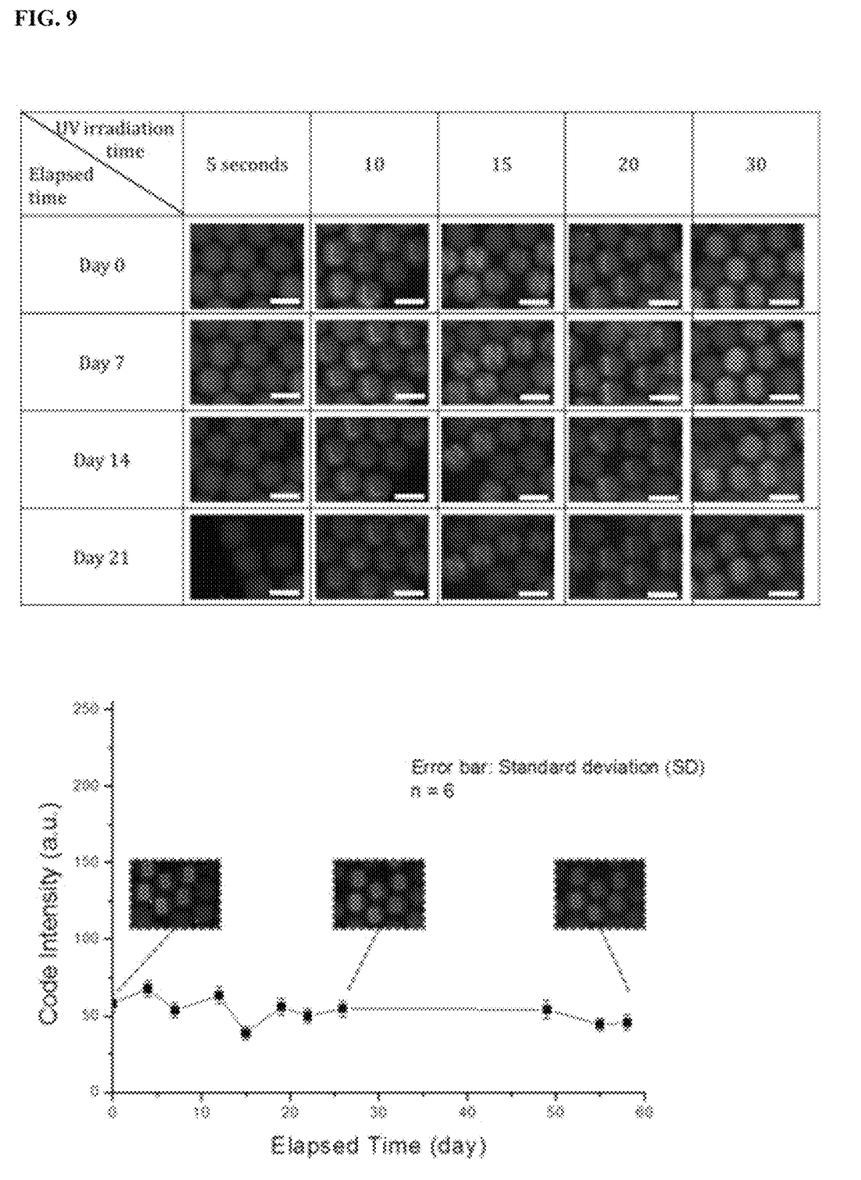
FIG. 9 shows code durability test results.

The codes of the encoded microcapsules should have long durability in order to generate a library of the encoded microcapsules. FIG. 9 shows code durability test results. Referring to FIG. 9, the ultraviolet light irradiation time was varied to identify whether the codes were sustained in the encoded microcapsules after storage for a long time. As a result, it was confirmed that the fluorescent intensities of the codes were maintained constant for 20 days or more.

According to one embodiment of the present disclosure, a microarray using the encoded microcapsules is provided. The microarray can be fabricated by introducing microcapsules, which are encoded so as to be distinguished from each other depending on the kind of target substances included therein, into a substrate with microwells, and breaking the microcapsules to release core liquids including the target substances from the microcapsules. Each of the microcapsules has a hydrophilic liquid core including the target substance and a hydrophobic shell surrounding the liquid core. Graphical codes are introduced on the surface of the shell.

According to one embodiment of the present disclosure, an assay method is provided that uses the microcapsules encoded so as to be distinguished from each other depending on the kind of target substances included therein. The assay method includes: introducing the encoded microcapsules into a substrate with microwells; reading the codes of the encoded microcapsules arranged inside the microwells; introducing analytes into the microwells; and breaking the microcapsules introduced into the microwells to allow the target substances to react with the analytes. The target substances include drugs and are sealed by the microcapsules. The microcapsules are assembled in the microwells of the substrate. Graphical codes engraved on the shell portions of the microcapsules can be read to determine what target substances are contained in the capsules. The graphical codes may be read, for example, by image processing. Fluorescent images of the microcapsules are taken through a microscope and are analyzed by an image processing algorithm. Due to this analysis, characters or figure patterns can be automatically recognized to read the graphical codes. The encoded microcapsules are placed on the microwells and assembled in the microwells by simply sweeping with a suitable tool, for example, a planar plate like glass. By modifying the design of the microwells, different numbers of the microcapsules can be assembled in each independent reaction space.

Preferably, the method further includes forming layers of a liquid immiscible with the liquids inside the microcapsules introduced into the microwells, on the microwells such that the microwells are distinguished from each other as independent reaction spaces. After assembly of the microcapsules, a liquid like oil immiscible with water is poured on the microwells such that the microwells have isolated environments. As a result, the microwells act as independent reaction spaces without cross-contamination. Thereafter, the assembled microcapsules are broken using micropillars, etc. disposed corresponding to the microwells, so that the liquids inside the capsules can be released to react with surrounding substances. The microcapsules may be broken in such a manner that the substrate is bonded and pressed to an extra substrate with micropillars disposed corresponding to the microwells.

Figure 10:
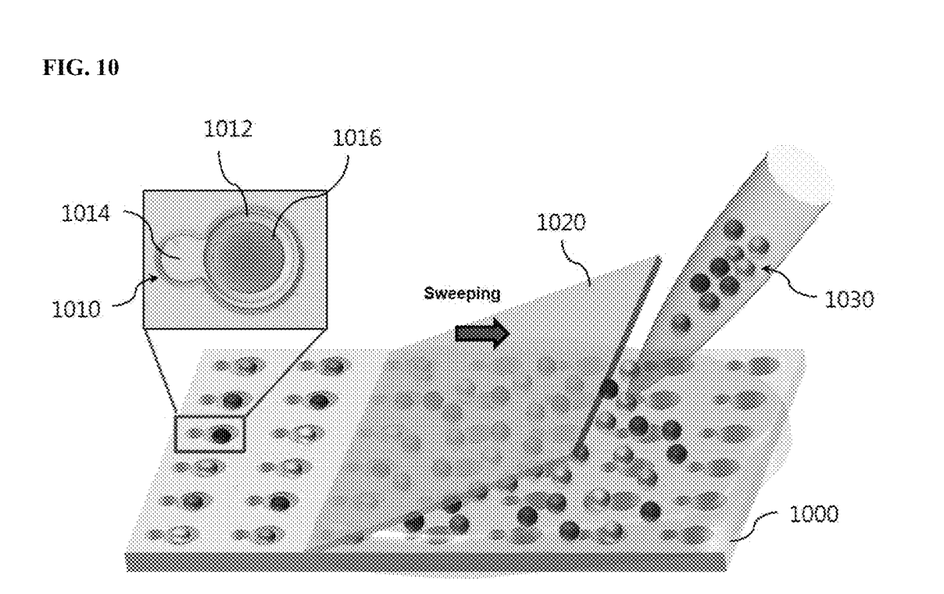
FIG. 10 shows a process for assembling encoded microcapsules in a substrate with microwells.

FIG. 10 shows a process for assembling encoded microcapsules in a substrate with microwells. Referring to FIG. 10, microwells 1010 accommodating microcapsules 1016 are aligned on a substrate 1000. Each microwell 1010 has a size to accommodate one microcapsule 1016. The microcapsules 1016 are dispensed from a library 1030 thereof and are introduced into the microwells 1010. Each microwell 1010 consists of a microcapsule well 1012 and a reaction well 1014. The microcapsule 1016 is assembled in the microcapsule well 1012. In the reaction well 1014, the reaction of the liquid released from the capsule can be observed. The microcapsules are dispensed on the substrate 1000 and simply swept with a planar plate (e.g., cover glass). By a few sweeping, the microcapsules 1016 are assembled in the microwells.

Figure 11:
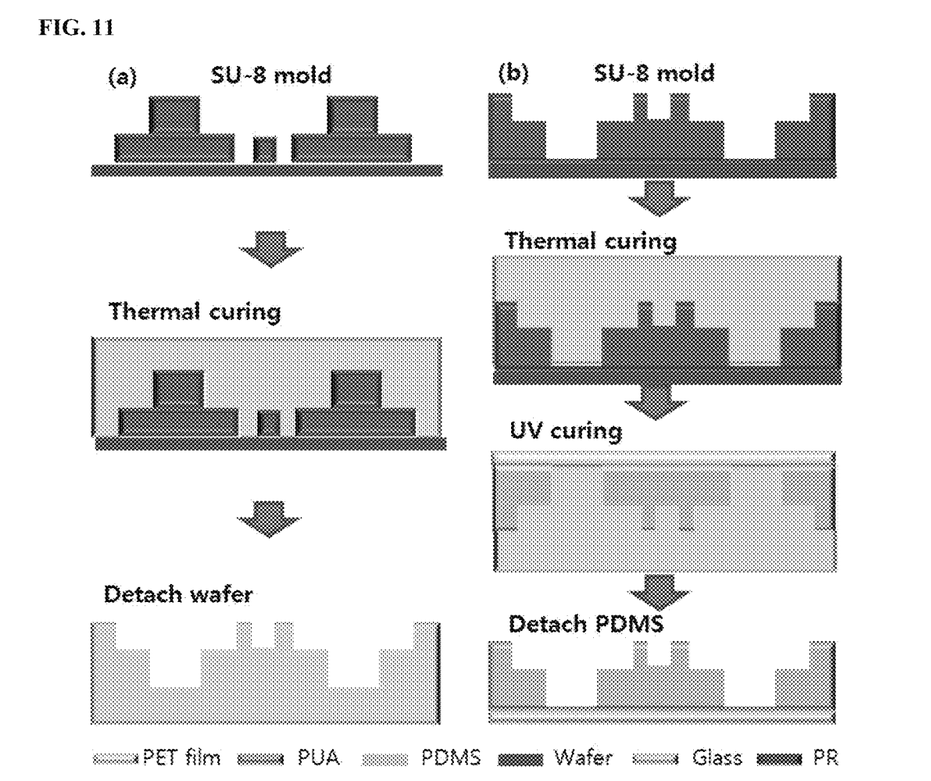
FIG. 11 shows microwell fabrication processes using (a) PDMS and (b) PUA.

The substrate with microwells can be constructed, for example, by the following two methods. One method is using polydimethylsiloxane (PDMS). According to this method, PDMS is poured onto a wafer that is microwell-patterned with a photoresist (SU-8) and thermally cured. After curing, the cured PDMS is peeled off from the wafer. The other method is using polyurethane acrylate (PUA). PUA microwells have hard surfaces, unlike elastic PDMS. The PUA microwells can be made by the following procedure. First, a liquid PUA monomer is poured on a PDMS structure and a transparent substrate such as an adhesion primer coated glass is placed thereon. Upon irradiation with ultraviolet light, the PUA monomer is cured and attached to the substrate. Thereafter, removal of the PDMS structure leaves microwells deposited on the transparent substrate. Since the PUA microwell fabrication involves one-time PDMS molding, the pattern of the photoresist deposited on the wafer has a reversed phase to that of the PDMS microwells. FIG. 11 shows the microwell fabrication processes using (a) PDMS and (b) PUA.

Figure 12:
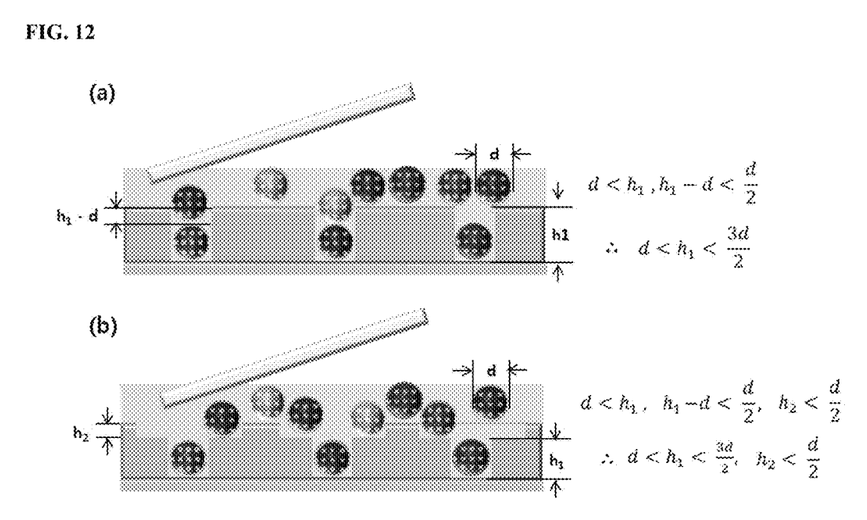
FIG. 12 shows exemplary microwells whose depths are suitably dimensioned depending on the size of microcapsules.

Each of the microwells may consist of one or two layers. FIG. 12 shows exemplary microwells whose depths are suitably dimensioned depending on the size of microcapsules. (a) and (b) of FIG. 12 show one-layer microwells and two-layer microwells, respectively. Referring to FIG. 12, for example, in the case of the one-layer microwell, the height of the microwell (h1) should be higher than the diameter of the microcapsule (d) and smaller than one and a half diameter of the microcapsule, which enables extra microcapsules to be removed easily by sweeping after assembly of microcapsules. For example, in the case of the two-layer microwell, the height (h1) of the bottom layer is the same with the height of the one-layer microwell and the height (h2) of the top layer should be smaller than a half of the diameter of the microcapsule for the same reason.

Figure 13:
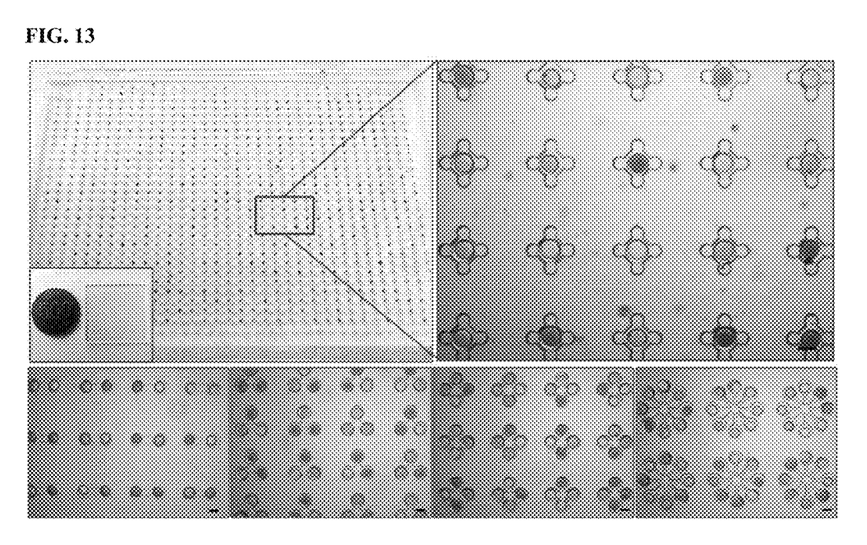
FIG. 13 shows microwells with various patterns.

In some embodiments, the microwells may be made in various patterns using photolithography. For example, the microwells may be designed such that one microcapsule is assembled in one reaction space. Alternatively, the microwells may be designed such that several microcapsules may be assembled in one reaction space. Due to this design, reactions of a combination of various drugs can be observed. FIG. 13 shows microwells with various patterns. As can be seen from FIG. 13, the microcapsules are assembled in various microwell arrays. The top images of FIG. 13 are a microwell array and a magnification image thereof. In the inset of the top left image, the overall size of the microwell array is compared with the size of a coin. The bottom images show various patterns of the microwells. Scale bars indicate 200 μm.

Figure 14:
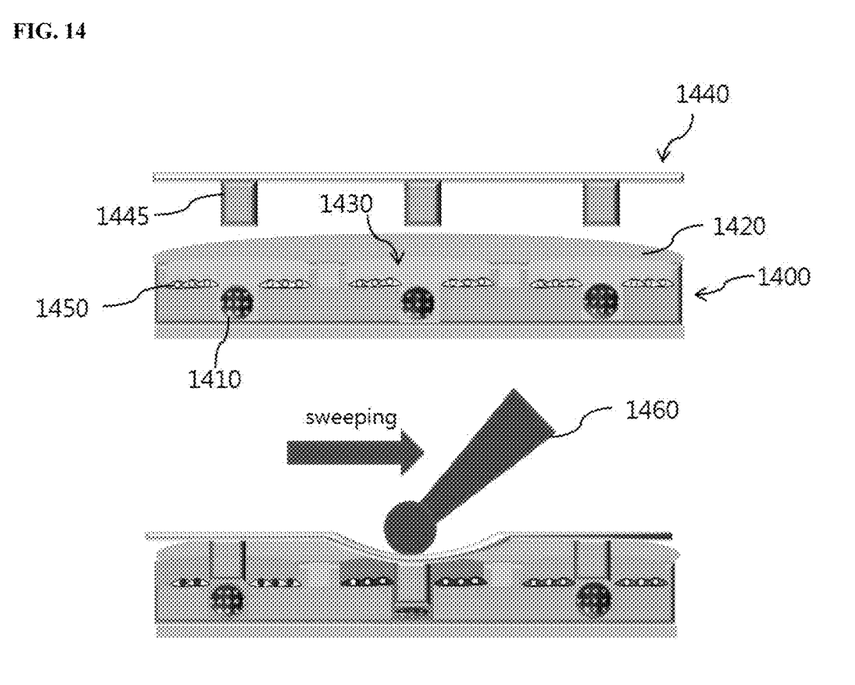
FIG. 14 shows the release process of core liquids from microcapsules assembled in microwells.

Thereafter, the assembled microcapsules are broken to release core liquids therefrom. FIG. 14 shows the release process of core liquids from the microcapsules assembled in the microwells. Referring to the top view of FIG. 14, a microwell array 1400 has microwells 1430 in which microcapsules 1410 are assembled, and an analyte 1450 is arranged in each microwell 1430. A liquid 1420 like oil immiscible with water may be poured on the microwells 1430 to allow the microwells 1430 to act as independent reaction spaces. Thereafter, a substrate 1440 in which micropillars 1445 are aligned corresponding to the microwells 1430 is arranged such that the micropillars 1445 match the respective microwells 1430. The microcapsules 1410 are physically broken by pushing the substrate 1440 with a suitable tool 1460 such as a roller. As a result, the liquids are released from the microcapsules and react with the analytes 1450. For example, in the case of drug screening using cells, cells are allowed to grow in the microwells, the microcapsules are assembled in the microwells, and the liquids are released from the capsules to allow the drugs to react with the cells. From the reactions, the toxicity of the drugs to the cells can be assayed. In the case of enzymatic assay, a substrate and an inhibitor, etc. are put in the microcapsules without cells, an enzyme is filled in the microwells outside the capsules, and the liquids are released from the capsules to determine how the catalytic reaction of the enzyme is inhibited depending on the kind of the inhibitor.

The micropillar array can be fabricated by irradiating PUA pillars on a flexible substrate (e.g., a PET film) with ultraviolet light. The fabrication process is the same as that of PUA microwells except that a flexible substrate is used instead of a hard substrate such as glass. Specifically, liquid PUA is poured on a PDMS mold, a flexible film is placed thereon, followed by irradiation with ultraviolet light. As a result of the curing, the PUA is adhered to the film to create PUA micropillars having a pattern corresponding to that of the PDMS mold.

Various analyses are enabled by the use of the encoded microcapsules and the substrate with microwells. For example, an anticancer drug-induced apoptosis test may be conducted using the substrate with microwells. First, cells are allowed to grow in the microwells. Thereafter, the encoded microcapsules containing different drugs are assembled in the microwells. The codes of the microcapsules can be read to determine what drugs are contained in the microwells. Then, oil is used to isolate the microwells and the micropillar array is used to release the liquids from the capsules. As a result, a liquid microarray is fabricated. After incubation in an incubator for 12 to 24 hours, an apoptosis detection kit is placed on the microwells to react with the cells. Fluorescent images are observed to identify how many cells are dead and alive depending on the kind and concentration of the drugs.

Figure 15:
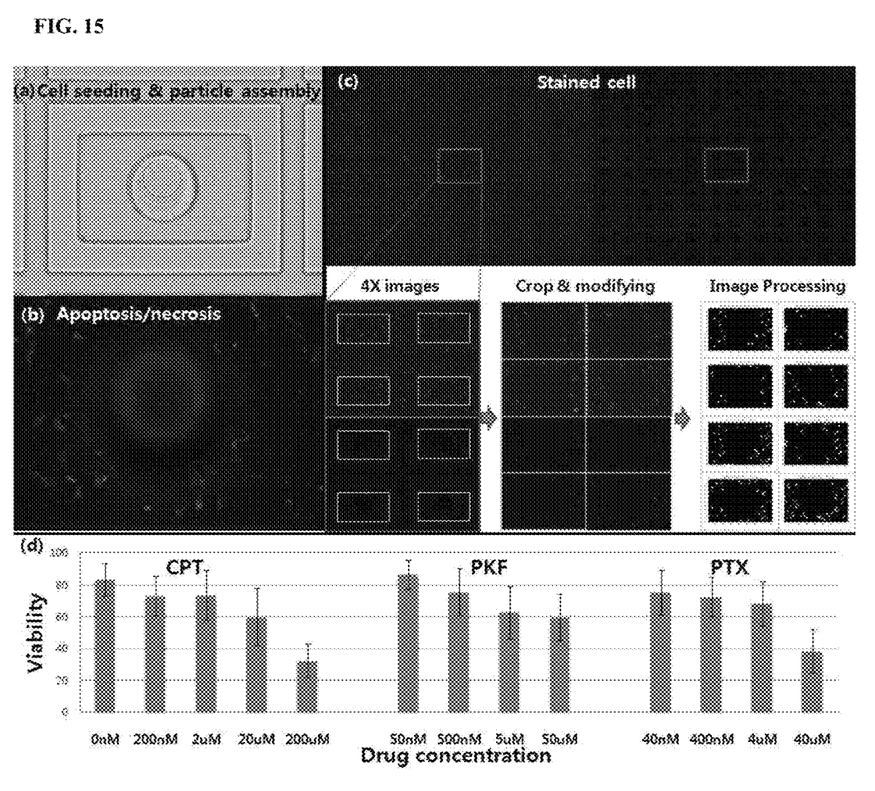
FIG. 15 shows the results of drug-induced apoptosis test using anticancer drugs.

FIG. 15 shows the results of drug-induced apoptosis test using anticancer drugs. (a)-(d) of FIG. 15 show (a) a microcapsule assembled in the microwell and cells, (b) fluorescent images of apoptosis after reactions with drugs, (c) large-area data processing by image processing, and (d) viability test results for different drugs with various concentrations, respectively. The drugs are camptothecin (CPT), toxoflavin (PKF), and paclitaxel (PTX). Referring to FIG. 15, the degrees of apoptosis for the different drugs with various concentrations can be understood using one liquid microarray.

According to the foregoing embodiments of the present disclosure, various kinds of drug candidates can be put in the microcapsules and made physically independent. The present disclosure can utilize a particle-based handling process by which a small amount of liquid can be handled in a parallel and effective manner, compared to a conventional serial liquid handling process using pipettes. In addition, graphical codes can be formed in a simple manner without the need for special coding materials like fluorescent dyes or quantum dots, which are used in conventional spectral coding. Therefore, the encoded microcapsules can be produced at reduced cost. According to the method of the present disclosure, codes consisting of characters or figures can be formed. Therefore, in comparison with conventional spectral coding, the method of the present disclosure can innovatively increase the number of codes, enabling the formation of a microcapsule library. Thus, dramatically increasing drug candidates as a result of the rapid technological advances can be effectively handled.

Parallel drug screening is enabled by the use of the liquid microarray of the present disclosure, which is fabricated by assembling the microcapsules in the microwells and releasing liquids from the capsules. According to the present disclosure, the number of data obtainable from one image increases because reactions occur in the micrometer-scale spaces. The consumption of drugs can be drastically reduced compared to that of drugs in conventional plate-based screening techniques. Therefore, the present disclosure is advantageous from an economic viewpoint. The microwells can be designed such that several microcapsules are assembled in one independent reaction space. Due to this design, reactions of a combination of various drugs can be easily observed.

What is claimed is:
1. Microcapsules encoded depending on a kind of a target substance present therein, comprising:
a hydrophilic liquid core comprising the target substance;
a hydrophobic shell surrounding the liquid core, the hydrophobic shell comprising a photoinitiator,
wherein the photoinitiator has a chromophore capable of emitting fluorescence after decomposition of the photoinitiator; and graphical codes engraved on a surface of the hydrophobic shell so that the microcapsules are encoded in order to distinguish from each other depending on the kind of the target substance being included in the hydrophilic liquid core wherein each of the graphical codes emits florescent light at a higher intensity than the rest of the surface of the hydrophobic shell.

2. The encoded microcapsules according to claim 1, wherein the target substance is a chemical substance or a biological substance.

3. The encoded microcapsules according to claim 2, wherein the chemical substance is a drug or the biological substance is selected from the group consisting of cells, molecules, proteins, bacteria, DNAs, RNAs, and combinations thereof.

4. The encoded microcapsules according to claim 1, wherein the liquid core is a water droplet.

5. The encoded microcapsules according to claim 1, wherein the shell is formed by curing a photocurable polymer in the presence of the photoinitiator.

6. The encoded microcapsules according to claim 1, wherein the graphical codes contain a fluorescent material derived from the photoinitiator.

7. A method of producing encoded microcapsules, the method comprising:
    preparing double emulsion droplets, each of which has a hydrophilic liquid core comprising a target substance and a hydrophobic shell surrounding the liquid core, wherein the hydrophobic shell contains a photocurable polymer and a photoinitiator having a chromophore;
    by an external energy source, curing the photocurable polymer to form core-shell structured microcapsules; and
    engraving graphical codes on a surface of the hydrophobic shell by irradiating patterned energy on the cured core shell microcapsules and distinguishing among individual microcapsules by fluorescence emitted from the chromophore of the photoinitiator in the engraved region of the surface,
    wherein the photoinitiator includes a moiety capable of being decomposed by an external energy source and the chromophore is capable of emitting the fluorescence after decomposition of the photoinitiator.

8. The method according to claim 7, wherein the photoinitiator is 2,2-dimethoxy-2-phenylacetophenone.

9. The method according to claim 7, wherein the double emulsion droplets are prepared using a microfluidic chip comprising a channel area having a hydrophobic surface and a channel area having a hydrophilic surface.

10. The method according to claim 7, wherein the patterned energy is irradiated through a digital micromirror device (DMD).

11. The method according to claim 7, wherein the patterned energy is irradiated by lithography using a mask.

12. The method according to claim 11, wherein the patterned energy is irradiated in a bi-directional encoding manner using two masks interposing the microcapsules therebetween.

13. The method according to claim 11, wherein the patterned energy is irradiated in such a manner that the mask and a planar substrate are arranged to face each other through the microcapsules, pressed to each other, followed by bi-directional encoding.

14. An assay method using microcapsules encoded so as to be distinguished from each other depending on the kind of target substances present therein, the method comprising:
    introducing the encoded microcapsules of claim 1 into a substrate of microwells; reading the codes of the encoded microcapsules arranged inside the microwells; introducing analytes into the microwells; and
    breaking the microcapsules introduced into the microwells to allow the target substances to react with the analytes.

15. The assay method according to claim 14, further comprising forming layers of a liquid immiscible with the liquids inside the microcapsules introduced into the microwells, on the microwells such that the microwells are distinguished from each other as independent reaction spaces.

16. The assay method according to claim 14, wherein the microcapsules are broken in such a manner that the substrate is bonded and pressed to an extra substrate with micropillars disposed corresponding to the microwells.

17. A microarray, comprising:
    microcapsules encoded to be distinguished from each other depending on a kind of target substances;
    a substrate having microwells, wherein said microcapsules are introduced in the substrate; and
    core liquids having the target substances being released when the microcapsules are broken,
    wherein each of the microcapsules, comprises;
    a hydrophilic liquid core comprising the target substances,
    a hydrophobic shell surrounding the liquid core, the hydrophobic shell comprising a photoinitiator,
    wherein the photoinitiator has a chromophore capable of emitting fluorescence after decomposition of the photoinitiator, and
    graphical codes engraved on a surface of the hydrophobic shell so that the microcapsules are encoded in order to distinguish from each other depending on the kind of the target substance being included in the hydrophilic liquid core
    wherein each of the graphical codes emits florescent light at a higher intensity than the rest of the surface of the hydrophobic shell.

* * * * *